United States Patent [19]

Erpenbach et al.

[11] Patent Number: 5,124,290
[45] Date of Patent: Jun. 23, 1992

[54] PROCESS FOR REMOVING METALLIC CORROSION PRODUCTS FROM CARBONYLATION REACTIONS CARRIED OUT UNDER ANHYDROUS CONDITIONS

[75] Inventors: Heinz Erpenbach, Cologne; Reinhard Gradl, Erftstadt; Erhard J',uml/a/gers, Bornheim; Andreas Seidel, Cologne; Peter Prinz, Hürth, all of Fed. Rep. of Germany

[73] Assignee: Hoechst Aktiengesellschaft, Frankfurt am Main, Fed. Rep. of Germany

[21] Appl. No.: 777,066

[22] Filed: Oct. 16, 1991

[30] Foreign Application Priority Data

Oct. 30, 1990 [DE] Fed. Rep. of Germany ....... 4034501

[51] Int. Cl.$^5$ .................. B01J 38/74; B01J 31/40; C07C 5/12; C07C 53/08
[52] U.S. Cl. ........................ 502/12; 502/24; 560/232; 562/519; 562/891
[58] Field of Search ................. 502/12, 24; 562/519, 562/891; 560/232; 423/22, 54, 139

[56] References Cited

U.S. PATENT DOCUMENTS

| | | | |
|---|---|---|---|
| 4,007,130 | 2/1977 | Leach et al. | 502/12 |
| 4,113,754 | 9/1978 | Kummer et al. | 502/12 |
| 4,894,477 | 1/1990 | Scates et al. | 502/12 |
| 4,985,383 | 1/1991 | Erpenbach et al. | 502/24 |

FOREIGN PATENT DOCUMENTS

| | | |
|---|---|---|
| 1258469 | 8/1989 | Canada . |
| 0265140 | 4/1988 | European Pat. Off. . |
| 2311388 | 9/1974 | Fed. Rep. of Germany ........ 502/24 |
| 3429179 | 2/1986 | Fed. Rep. of Germany . |

Primary Examiner—Paul E. Konopka
Attorney, Agent, or Firm—Connolly and Hutz

[57] ABSTRACT

A process for removing metallic corrosion products from carbonylation reactions which are carried out under anhydrous conditions and in which methyl acetate and/or methanol and/or dimethyl ether are reacted over a noble metal catalyst system which comprises a noble metal of group VIII of the periodic table of the elements, a co-catalyst, such as iodide or bromide, in particular methyl iodide, and a promoter, such as an organophosphonium or organoammonium salt, and if appropriate a lithium salt, to give acetic acid and/or acetic anhydride is described, the process comprising a) bringing the reaction solution which is contaminated with metallic corrosion products and contains the catalyst system into contact with an ion exchanger;

b) separating this reaction solution which has been brought into contact in this way from the ion exchanger;

c) desorbing the promoter adsorbed on the ion exchanger before regeneration with acetic acid and/or acetic anhydride;

d) combining the eluate obtained in step c) with the reaction solution separated off in step b) and recycling the components together into the carbonylation reaction;

e) regenerating the ion exchanger obtained from step c) with a strong mineral acid; and f) washing the ion exchanger regenerated in this way with acetic acid and/or acetic anhydride until free from water, before use in step a).

12 Claims, No Drawings

PROCESS FOR REMOVING METALLIC CORROSION PRODUCTS FROM CARBONYLATION REACTIONS CARRIED OUT UNDER ANHYDROUS CONDITIONS

The invention relates to a process for removing metallic corrosion products from carbonylation reactions which are carried out under anhydrous conditions and in which methyl acetate and/or methanol and/or dimethyl ether are reacted over a noble metal catalyst system, which comprises a noble metal of group VIII of the periodic table of the elements, a co-catalyst, such as iodide or bromide, in particular methyl iodide, and a promoter, such as an organophosphonium or organoammonium salt, and if appropriate a lithium salt, to give acetic acid and/or acetic anhydride.

For economic reasons, the proportion of acetic acid and acetic anhydride production prepared by carbonylation is increasing constantly. It is important here for the expensive noble metals and organophosphonium and organo-ammonium salts to be used without losses.

It has been found that metallic corrosion products, such as iron, nickel, chromium and molybdenum, become concentrated in the reaction solution passed in circulation. This results in a deterioration of the activity of the catalyst system.

The expert therefore has the object of removing metallic corrosion products from the reaction solution without losses in catalyst constituents A process for the removal of metallic corrosion products by means of an ion exchanger is described in US-A-4,007,130. The metallic corrosion products are adsorbed onto the ion exchanger and the noble metals remain in the eluate and can be recycled directly as a catalyst solution Residual amounts of catalyst are rinsed into the catalyst solution with water, before the ion exchanger laden with metallic corrosion products is regenerated with mineral acids.

It has been found that this process cannot be applied to anhydrous carbonylation reactions which contain organophosphonium or organoammonium iodide as a promoter, since the promoters are also adsorbed onto the ion exchanger. For the carbonylation to be carried out economically, however, recovery both of the noble metals and of the promoter is necessary. The catalyst cannot be eluted with water, as is envisaged in US-A-4,007,130, since anhydrous conditions must be used to avoid an increased corrosion in the carbonylation process (DE-A-3 429 179 ≙ 258 469).

The disadvantages described in the prior art can be avoided by the process according to the invention. The metallic corrosion products are removed by means of an ion exchange process such that both the noble metals and the organophosphonium or organoammonium compounds can be recycled, as the catalyst system and without further working up, to the circulation of the reaction solution of a carbonylation carried out under anhydrous conditions.

In detail, the invention comprises
a) bringing the reaction solution which is contaminated with metallic corrosion products and contains the catalyst system into contact with an ion exchanger;
b) separating this reaction solution which has been brought into contact in this way from the ion exchanger;
c) desorbing the promoter adsorbed on the ion exchanger before regeneration with acetic acid and/or acetic anhydride;
d) combining the eluate obtained in step c) with the reaction solution separated off in step b) and recycling the components together into the carbonylation reaction;
e) regenerating the ion exchanger obtained from step c) with a strong mineral acid; and
f) washing the ion exchanger regenerated in this way with acetic acid and/or acetic anhydride until free from water, before use in step a).

The process according to the invention can furthermore preferably and optionally comprise
aa) using a strongly acid macroporous ion exchanger which comprises a styrene/divinylbenzene polymer comprising sulfonic acid groups;
bb) carrying out step a) at temperatures between 20° and 120° C., in particular 75° and 100° C., under pressures from 1 to 10 bar;
cc) passing the contaminated reaction solution through a fixed ion exchanger bed;
dd) treating the contaminated reaction solution with the ion exchanger in a fluidized bed;
ee) treating the contaminated reaction solution with the ion exchanger batchwise in a stirred container; and
ff) using 0.5 to 5, in particular 1 to 3 molar hydriodic acid, sulfuric acid or hydrochloric acid as the strong mineral acid in step e).

The catalyst system contains rhodium compounds and iridium compounds, in particular, as the noble metal. In addition to methyl iodide, elemental iodine or hydrogen iodide can furthermore also be used as the co-catalyst.

Promoters which are added are, in particular, quaternary phosphonium salts, such as methyltributylphosphonium, methyltriphenylphosphonium, tetrabutylphosphonium or dimethyldibutylphosphonium iodide, as well as N,N-dimethyl-imidazolium, N-methyl-3-picolinium or methylquinolinium iodide.

A molar ratio of noble metal to methyl iodide to promoter to methyl acetate/methanol/dimethyl ether mixture of 1:(10–300) : (2–100) : (10–1000) at a noble metal concentration of 0.005 to 0.05 mol/l has proved to be appropriate in the carbonylation reaction.

®Amberlyst 15 (Rohm and Haas Deutschland GmbH, 6000 Frankfurt 1) and ®Lewatit SPC 112 and SPC 118 (Bayer AG, 5090 Leverkusen-Bayerwerk) can be used as the strongly acid macroporous ion exchangers.

Before removal of the metallic corrosion products from the reaction solution, a proportion of the carbonylation products (acetic acid, acetic anhydride) is separated off from the reaction solution by distillation. The distillation bottom product then brought into contact with the ion exchanger contains

| | |
|---|---|
| 30 to 65% by weight of | promoter (methyltributylphosphonium iodide) |
| 25 to 60% by weight of | organic compound (acetic acid, acetic anhydride, ethylidene diacetate) |
| 2 to 15% by weight of | rhodiumcarbonyl complex [Rh(CO)$_2$I$_2$] [CH$_3$P(C$_4$H$_9$)$_3$] |
| 0.5 to 1.0% by weight of Fe | in the form of soluble compounds |
| 0.05 to 0.5% by weight of Cr | |
| 0.03 to 0.3% by weight of Ni | |

0.01 to 0.1% by weight of Mo

EXAMPLE 1

120 ml of ®Lewatit SPC 118 in the H+ form were covered with a layer of an acetic acid/acetic anhydride mixture (1 : 1 parts by volume) and kept overnight to swell. For the adsorption, the ion exchanger together with the supernatant liquid was packed into a column (20 mm φ and 400 mm length) heated with a jacket and heated up to 80° C. 700 g of contaminated reaction solution which had been concentrated by distillation were passed over the ion exchanger at this temperature at a flow rate of 20 ml/minute. The reaction solution contained: 31.01% by weight of acetic acid, 11.00% by weight of acetic anhydride, 29.58% by weight of methyltributylphosphonium-iodide, 22.63% by weight of non-specified organic phase and 5.78% by weight of metal salts, including the rhodium complex.

After the catalyst solution had drained off completely, the ion exchanger laden with the corrosion products was treated with 500 ml of an acetic acid/acetic anhydride mixture (19 : 1 parts by volume) at 80° C. The eluate was combined with the purified reaction solution. The laden ion exchanger treated with acetic acid/acetic anhydride was regenerated with 1000 g of 1.5 molar hydrochloric acid at 23° C. The amount of desorbed metals in the eluate obtained by this procedure was determined.

The ad- and desorption rates of the various metals are recorded in Table 1. The eluate of the acetic acid/acetic anhydride treatment contained 8% by weight of methyltributylphosphonium salt.

TABLE 1

| Element | Reaction solution before treatment with ion exchanger [% by weight] | Adsorption rate [%] | Desorption rate [%] |
| --- | --- | --- | --- |
| Rh | 0.34 | 0.0 | — |
| Fe | 0.15 | 85.3 | 100 |
| Ni | 0.22 | 62.3 | 100 |
| Cr | 0.07 | 0.6 | 100 |
| Mn | 0.01 | 100.0 | 87 |
| Mo | 0.07 | 78.0 | 5 |

The adsorption rate was determined mathematically from the analytical data:

$$[\%] \text{ Adsorption rate} = \frac{\text{Amount of metal salt after ion exchanger treatment}}{\text{Amount of metal salt before ion exchanger treatment}} \times 100$$

The desorption rate was determined mathematically:

$$[\%] \text{ Desorption rate} = \frac{\text{Amount of metal salt before ion exchanger treatment minus amount of metal salt after ion exchanger treatment}}{\text{Amount of metal salt in the mineral acid eluate}} \times 100$$

EXAMPLE 2

1000 ml of ®Lewatit SPC 112 in the H+ form were heated up to a temperature of 95° C. as in Example 1 with an acetic acid/acetic anhydride mixture in a column (70 mm φ and 300 mm length), heated with a jacket, under a pressure of 1.5 bar. 9500 g of contaminated reaction solution which had been concentrated by distillation were passed over the ion exchanger at this temperature at a flow rate of 80 ml/minute. The reaction solution contained: 31.01% by weight of acetic acid, 11.00% by weight of acetic anhydride, 30.88% by weight of methyltributylphosphonium iodide, 22.63% by weight of non-specified organic phase and 4.48% by weight of metal salts.

After the catalyst solution had drained off completely, the laden ion exchanger was treated with 7000 ml of acetic acid at 95° C. The acetic acid eluate collected comprised 1.2% by weight of methyltributylphosphonium salt.

After the acetic acid treatment, 2800 ml of 3 molar sulfuric acid were passed over the ion exchanger at 23° C. at a flow rate of 30 ml/minute. The desorbed metal salts were determined analytically in this eluate.

TABLE 2

| Element | Reaction solution before treatment with ion exchanger [% by weight] | Adsorption rate [%] | Desorption rate [%] |
| --- | --- | --- | --- |
| Rh | 0.35 | 0.0 | — |
| Fe | 0.16 | 52.7 | 94 |
| Ni | 0.06 | 44.0 | 83 |
| Cr | 0.01 | 16.0 | 100 |
| Mn | 0.01 | 31.0 | 100 |
| Mo | 0.06 | 17.8 | 36 |

EXAMPLE 3

The ion exchanger regenerated in Example 2 was rinsed until free from water by treatment with 2000 ml of acetic acid at 45° C. This ion exchanger was used in accordance with Example 2. The results are summarized in Table 3.

TABLE 3

| Element | Reaction solution before treatment with ion exchanger [% by weight] | Adsorption rate [%] | Desorption rate [%] |
| --- | --- | --- | --- |
| Rh | 0.36 | 0.0 | — |
| Fe | 0.08 | 64.7 | 99 |
| Ni | 0.04 | 48.5 | 75 |
| Cr | 0.01 | 6.7 | 100 |
| Mn | 0.05 | 6.8 | 53 |

We claim:

1. A process for removing metallic corrosion products from the reaction solution of a carbonylation reaction carried out under anhydrous conditions, in which methyl acetate or methanol or dimethyl ether or a mixture thereof is reacted over a noble metal catalyst system to give acetic acid and acetic anhydride, the noble metal catalyst system consisting of a noble metal of group VIII of the periodic table of the elements, a co-catalyst chosen from the group comprising iodide and bromide and a promoter chosen from the group comprising organophosphonium salts and organoammonium salts, which comprises:

a) bringing the reaction solution which is contaminated with metallic corrosion products and contains the catalyst system into contact with an ion exchanger;

b) separating the reaction solution brought into contact from the ion exchanger;

c) desorbing the promoter adsorbed on the ion exchanger before regeneration with acetic acid or acetic anhydride;

d) combining the eluate obtained in step c) with the reaction solution separated off in step b) and recycling the two together into the carbonylation reaction;

e) regenerating the ion exchanger obtained in step c) with a strong mineral acid; and f) washing the ion exchanger regenerated in this way with acetic acid or acetic anhydride until free from water, before use in step a).

2. The process as claimed in claim 1, wherein methyliodide is used as the co-catalyst.

3. The process as claimed in claim 1, wherein the noble metal catalyst system additionally contains a lithium salt.

4. The process as claimed in claim 1, wherein a strongly acid macroporous ion exchanger which comprises a styrene/divinylbenzene polymer comprising sulfonic acid groups is employed.

5. The process as claimed in claim 1, wherein step a) is carried out at a temperature between 20° and 120° C. under a pressure of 1 to 10 bar.

6. The process as claimed in claim 1, wherein step a) is carried out at a temperature of 75° to 100° C.

7. The process as claimed in claim 1, wherein the contaminated reaction solution is passed through a fixed ion exchanger bed.

8. The process as claimed in claim 1, wherein the contaminated reaction solution is treated with the ion exchanger in a fluidized bed.

9. The process as claimed in claim 1, wherein the contaminated reaction solution is treated with the ion exchanger batchwise in a stirred container.

10. The process as claimed in claim 1, wherein a strong metal acid chosen from the group comprising hydriodic acid, sulfuric acid and hydrochloric acid is employed in step e).

11. The process as claimed in claim 10, wherein the strong mineral acid is 0.5 to 5 molar.

12. The process as claimed in claim 10, wherein the strong mineral acid is 1 to 3 molar.

* * * * *

UNITED STATES PATENT AND TRADEMARK OFFICE
CERTIFICATE OF CORRECTION

PATENT NO. : 5,124,290

DATED : June 23, 1992

INVENTOR(S) : Erpenbach et al

It is certified that error appears in the above-identified patent and that said Letters Patent is hereby corrected as shown below:

On the title page, under list of inventors [75], delete "Erhard J',uml/a/gers" and insert: --Erhard Jägers--.

Signed and Sealed this

Tenth Day of August, 1993

Attest:

*Attesting Officer*

MICHAEL K. KIRK

*Acting Commissioner of Patents and Trademarks*